United States Patent
Yang et al.

(10) Patent No.: US 10,486,135 B2
(45) Date of Patent: Nov. 26, 2019

(54) SUPER ABSORBENT RESIN HAVING IMPROVED SOLIDIFICATION RESISTANCE, AND METHOD FOR PREPARING SAME

(71) Applicant: LG Chem, Ltd., Seoul (KR)

(72) Inventors: Young-In Yang, Daejeon (KR); Young-Sam Kim, Daejeon (KR); Jun-Kyu Kim, Daejeon (KR); Bo-Hee Park, Daejeon (KR); Ung-Gu Kang, Daejeon (KR); Min-Gyu Kim, Daejeon (KR); Su-Jin Kim, Daejeon (KR)

(73) Assignee: LG Chem, Ltd. (KR)

( * ) Notice: Subject to any disclaimer, the term of this patent is extended or adjusted under 35 U.S.C. 154(b) by 271 days.

(21) Appl. No.: 15/305,230

(22) PCT Filed: Oct. 14, 2015

(86) PCT No.: PCT/KR2015/010867
§ 371 (c)(1),
(2) Date: Oct. 19, 2016

(87) PCT Pub. No.: WO2016/111447
PCT Pub. Date: Jul. 14, 2016

(65) Prior Publication Data
US 2017/0036191 A1    Feb. 9, 2017

(30) Foreign Application Priority Data
Jan. 7, 2015   (KR) .................. 10-2015-0001839

(51) Int. Cl.
*B01J 20/26* (2006.01)
*C08J 3/12* (2006.01)
(Continued)

(52) U.S. Cl.
CPC ............ *B01J 20/267* (2013.01); *A61L 15/60* (2013.01); *B01J 20/02* (2013.01);
(Continued)

(58) Field of Classification Search
None
See application file for complete search history.

(56) References Cited

U.S. PATENT DOCUMENTS

| | | |
|---|---|---|
| 5,087,656 A | 2/1992 | Yoshinaga et al. |
| 5,229,488 A | 7/1993 | Nagasuna et al. |

(Continued)

FOREIGN PATENT DOCUMENTS

| | | |
|---|---|---|
| CN | 102617781 A | 8/2012 |
| EP | 0441975 A1 | 8/1991 |

(Continued)

OTHER PUBLICATIONS

Supplementary European Search Report for EP Application No. 15877167, dated Dec. 20, 2017.

(Continued)

*Primary Examiner* — Joseph D Anthony
(74) *Attorney, Agent, or Firm* — Lerner, David, Littenberg, Krumholz & Mentlik, LLP (57) ABSTRACT

Disclosed are a superabsorbent polymer having improved anti-caking properties and a method of preparing the same, and the superabsorbent polymer having improved anti-caking properties includes a superabsorbent polymer, microparticles, and water, and to improve anti-caking properties of the superabsorbent polymer, the temperature of the superabsorbent polymer or water upon addition of water or the aging time upon stirring is adjusted, thereby preventing caking of the particles.

21 Claims, 5 Drawing Sheets

(51) Int. Cl.
    B01J 20/30      (2006.01)
    C08K 3/36       (2006.01)
    C08K 7/26       (2006.01)
    B01J 20/02      (2006.01)
    B01J 20/28      (2006.01)
    C08J 3/24       (2006.01)
    A61L 15/60      (2006.01)
    C08L 101/14     (2006.01)

(52) U.S. Cl.
    CPC ... *B01J 20/28016* (2013.01); *B01J 20/28047* (2013.01); *B01J 20/28061* (2013.01); *B01J 20/28064* (2013.01); *B01J 20/28066* (2013.01); *B01J 20/3042* (2013.01); *B01J 20/3085* (2013.01); *C08J 3/12* (2013.01); *C08J 3/124* (2013.01); *C08J 3/245* (2013.01); *B01J 2220/46* (2013.01); *B01J 2220/68* (2013.01); *C08J 2300/14* (2013.01); *C08J 2333/02* (2013.01); *C08L 101/14* (2013.01)

(56) References Cited

U.S. PATENT DOCUMENTS

| | | | |
|---|---|---|---|
| 6,124,391 A * | 9/2000 | Sun | A61L 15/18 523/223 |
| 9,555,393 B2 * | 1/2017 | Lee | B01J 20/28026 |
| 10,035,130 B2 * | 7/2018 | Kim | C08F 2/10 |
| 2005/0239942 A1 * | 10/2005 | Herfert | A61F 13/534 524/445 |
| 2005/0245393 A1 | 11/2005 | Herfert et al. | |
| 2007/0225160 A1 | 9/2007 | Kitano et al. | |
| 2008/0058747 A1 * | 3/2008 | Singh Kainth | A61F 13/15 604/368 |
| 2009/0023848 A1 * | 1/2009 | Ahmed | A61L 15/56 524/422 |
| 2013/0096000 A1 * | 4/2013 | Tian | A61L 15/18 502/402 |
| 2014/0051813 A1 | 2/2014 | Won et al. | |
| 2017/0036191 A1 * | 2/2017 | Yang | C08J 3/075 |
| 2017/0266641 A1 * | 9/2017 | Kim | C08F 2/10 |
| 2018/0237611 A1 * | 8/2018 | Yang | C08K 3/36 |
| 2018/0297012 A1 * | 10/2018 | Kim | C08J 3/03 |

FOREIGN PATENT DOCUMENTS

| | | |
|---|---|---|
| EP | 1736508 A1 | 12/2006 |
| EP | 3078678 A1 | 10/2016 |
| EP | 3243843 A1 | 11/2017 |
| JP | S61127710 A | 6/1986 |
| JP | H08253597 A | 10/1996 |
| JP | 02881739 B2 | 4/1999 |
| JP | 2888852 B2 | 5/1999 |
| JP | 3335721 B2 | 10/2002 |
| JP | 2008106218 A | 5/2008 |
| KR | 20070096831 A | 10/2007 |
| KR | 20120059169 A | 6/2012 |
| KR | 20120081113 A | 7/2012 |
| WO | 2015084059 A1 | 6/2015 |

OTHER PUBLICATIONS

International Search Report from PCT/KR2015/010867, dated Jan. 13, 2016.

\* cited by examiner

SUPER ABSORBENT RESIN HAVING IMPROVED SOLIDIFICATION RESISTANCE, AND METHOD FOR PREPARING SAME

CROSS-REFERENCE TO RELATED APPLICATION(S)

This application is a national phase entry under 35 U.S.C. § 371 of International Application No. PCT/KR2015/010867, filed Oct. 14, 2015, which claims priority from Korean Patent Application No. 10-2015-0001839, filed Jan. 07, 2015, the disclosures of which are hereby incorporated herein by reference.

BACKGROUND OF THE INVENTION

1. Technical Field

The present invention relates to a superabsorbent polymer having improved anti-caking properties and a method of preparing the same and, more particularly, to a superabsorbent polymer having improved anti-caking properties, which includes a superabsorbent polymer, microparticles, and water, and wherein to improve anti-caking properties of the superabsorbent polymer, the temperature of the superabsorbent polymer or water upon addition of water or the aging time upon stirring is adjusted, thereby preventing caking of the particles.

2. Description of the Related Art

Superabsorbent polymers (SAPs) are synthetic polymers able to absorb water about 500~1000 times their own weight. Such superabsorbent polymers have actually begun to be used for sanitary items, and are being currently widely utilized in not only hygiene products such as baby disposable diapers and menstrual sanitary pads, but also in gardening soil repair agents, water stop agents for civil construction, seeding sheets, freshness retaining agents in food distribution sectors, and fomentation materials. Compared to conventional absorbent materials, superabsorbent polymers have an outstanding absorption capacity and thus the market value thereof is increasing with the wider range of applications thereof. In particular, superabsorbent polymers having excellent water absorbability are mainly employed in hygiene products such as baby diapers and adult diapers. Furthermore, upon application to hygiene products, superabsorbent polymers present in the diapers play a role in absorbing and retaining urine. Meanwhile, in the course of producing diapers, superabsorbent polymers may undergo high pressure and physical impact, and thus the properties thereof may be remarkably deteriorated, resulting in poor diaper performance.

In this regard, Korean Patent Application Publication No. 2012-0081113 discloses a method of preparing an absorbent polymer including water-insoluble inorganic particles. However, such a conventional technique is problematic because surface stickiness of the superabsorbent polymer becomes high with an increase in moisture content on the surface thereof, undesirably incurring agglomeration, poor processability, and low productivity as mentioned above, thus making it difficult to satisfy both high moisture content and high processability.

Meanwhile, when water is added to the superabsorbent polymer at room temperature or at relatively low temperature, temporal limitations of water diffusion are imposed on the surface of the superabsorbent polymer. Thus, in order to reduce a caking phenomenon, the aging time of the unstable superabsorbent polymer containing water has to be increased, undesirably lowering productivity. Hence, there are required methods of uniformly adding water to the superabsorbent polymer without caking. Even when no caking occurs upon addition of water, caking has to be prevented under long-term loads. To this end, when water is introduced into the superabsorbent polymer, efficient techniques for preventing caking of the superabsorbent polymer while improving properties and imparting novel functionalities are needed.

SUMMARY OF THE INVENTION

Accordingly, the present invention has been made keeping in mind the problems encountered in the art, and an object of the present invention is to provide a superabsorbent polymer having improved anti-caking properties, wherein the surface of the superabsorbent polymer is modified and thus viscosity and agglomeration are not increased upon absorption of water, thereby maintaining the particle size and facilitating control of the process load, particle size, and properties in the preparation process due to no reduction in processability.

Another object of the present invention is to provide a superabsorbent polymer having improved anti-caking properties, wherein caking of the superabsorbent polymer may be remarkably decreased or may be prevented at raised temperature through temperature control upon addition of a large amount of water, rather than at room temperature, and also the aging time is adjusted, thus preventing caking thereof.

Therefore, the present invention is intended to provide a superabsorbent polymer having improved anti-caking properties, wherein caking of the particles of the superabsorbent polymer may be blocked during storage or transport of final products after addition of water to the superabsorbent polymer.

In order to accomplish the above objects, the present invention provides a superabsorbent polymer having improved anti-caking properties, comprising: a superabsorbent polymer (A), particles (B) having i) a BET specific surface area of 300~1500 $m^2/g$ and ii) a porosity of 50% or more, and water (C), wherein the particles (B) are contained in an amount of 0.0001~15.0 parts by weight based on 100 parts by weight of the superabsorbent polymer (A), and the water (C) is contained in an amount of 0.1~20.0 parts by weight based on 100 parts by weight of the superabsorbent polymer (A) and the particles (B), and at least one of heating treatment and aging time control treatment is performed.

In addition, the present invention provides a method of preparing a superabsorbent polymer having improved anti-caking properties, comprising: a) adding a superabsorbent polymer (A) with 0.0001~15.0 parts by weight of particles (B) having i) a BET specific surface area of 300~1500 $m^2/g$ and ii) a porosity of 50% or more, based on 100 parts by weight of the superabsorbent polymer (A); and b) adding the superabsorbent polymer (A) and the particles (B) obtained in a) with 0.1~20.0 parts by weight of water (C), based on 100 parts by weight of the superabsorbent polymer (A) and the particles (B), and performing at least one of heating treatment and aging time control treatment, yielding the superabsorbent polymer having improved anti-caking properties.

In existing processes, when water is added to a superabsorbent polymer at room temperature or at relatively low temperature, temporal limitations of water diffusion are imposed on the surface of the superabsorbent polymer, and thus the aging time of the unstable superabsorbent polymer containing water has to be prolonged to reduce caking thereof, undesirably lowering productivity. With the goal of solving such problems, in a superabsorbent polymer having improved anti-caking properties and a preparation method thereof according to the present invention, upon addition of water to improve anti-caking properties of the superabsorbent polymer, the temperature of the superabsorbent polymer, water or a stirrer is adjusted, or the aging time is adjusted, thereby preventing caking of the particles. As such, individual factors can be adjusted alone or in combination. Hence, caking of the superabsorbent polymer can be remarkably decreased or can be prevented at raised temperature through temperature control, rather than at room temperature. Furthermore, the aging time is adjusted, thus ensuring anti-caking.

Also, in the superabsorbent polymer having improved anti-caking properties according to the present invention, viscosity and agglomeration are not increased upon absorption of water through surface modification thereof, thus maintaining the particle size, ultimately facilitating control of the process load, particle size, and properties in the preparation process due to increased processability.

Therefore, according to the present invention, caking of the particles of the superabsorbent polymer can be advantageously blocked during storage or transport of final products after addition of water to the superabsorbent polymer.

DESCRIPTION OF THE SPECIFIC EMBODIMENTS

Hereinafter, a detailed description will be given of the present invention.

According to the present invention, a superabsorbent polymer having improved anti-caking properties comprises a superabsorbent polymer (A), particles (B) having i) a BET specific surface area of 300~1500 $m^2/g$ and ii) a porosity of 50% or more, and water (C), wherein the particles (B) are contained in an amount of 0.0001~15.0 parts by weight based on 100 parts by weight of the superabsorbent polymer (A), and the water (C) is contained in an amount of 0.1~20.0 parts by weight based on 100 parts by weight of the superabsorbent polymer (A) and the particles (B), and at least one of heating treatment and aging time control treatment is performed.

More specifically, the heating treatment may be conducted by heating, to 26~95° C., at least one selected from the group consisting of the superabsorbent polymer (A) and the particles (B); a stirrer; and water, and the temperature of the superabsorbent polymer and the microparticles, water, or the stirrer for use in stirring upon aging, may be adjusted. Given the above heating treatment range, caking of the particles after addition of water to the superabsorbent polymer may be decreased and thus the aging time may be reduced, compared to at a temperature of 15~25° C. This means that the process time is shortened and the preparation process may be simplified. If the heating temperature is lower than the lower limit, an effect of reducing the aging time cannot be obtained. In contrast, if the heating temperature is higher than the upper limit, the rate of absorption of the superabsorbent polymer may increase, thus evaporating water or making it difficult to attain uniform moisture content.

In an embodiment of the present invention, the temperature of the superabsorbent polymer (SAP) passed through a cooler and a classifer after surface crosslinking during the production process of the superabsorbent polymer amounts to 60~70° C. As such, when water is immediately added without the need for additionally raising the temperature of the superabsorbent polymer, the aforementioned effect may be exhibited, thus obviating the additional use of energy.

Also, the aging time control treatment is conducted by adding the superabsorbent polymer (A) and the particles (B) with water (C) at 15~25° C. and then aging the resulting mixture with stirring at 5~1500 rpm at 26~95° C. for 1~120 min. Given the above aging treatment range, no caking occurs in the procedures from addition of the superabsorbent polymer with water to packaging thereof.

Even when caking does not occur upon addition of water to the superabsorbent polymer, it may be caused under continuous loads for a long period of time, but prevention thereof is possible. If the aging time is shorter than the lower limit, caking of the particles may take place. In contrast, if the aging time is longer than the upper limit, economic benefits are negated due to unnecessary processing.

Also, when the heating treatment and the aging time control treatment are simultaneously carried out, at least one selected from the group consisting of the superabsorbent polymer (A) and the particles (B); the stirrer; and water is heated to 26~95° C., and then aged with stirring at 5~1500 rpm at 15~25° C. for 1~120 min. As such, there are no significant changes in properties such as particle size distribution, flowability and bulk density depending on the aging time. This means that addition of water to the superabsorbent polymer at raised temperature results in remarkably decreased aging time, compared to addition of water at room temperature.

Whereas, even when water is added to the superabsorbent polymer at 15~25° C. corresponding to room temperature, caking may not occur under the condition that the aging time is increased. However, an increase in the aging time may undesirably lead to lowered productivity.

In the superabsorbent polymer having improved anti-caking properties, the particles (B) having the properties of i) and ii) are preferably added in an amount of 0.0001~15.0 parts by weight, more preferably 0.001~2.0 parts by weight, and still more preferably 0.05~0.15 parts by weight, based on 100 parts by weight of the superabsorbent polymer (A).

If the amount of the particles (B) is less than the lower limit, desired effects fail to be obtained. In contrast, if the amount thereof exceeds the upper limit, economic benefits may be negated due to the excessive use of the particles (B).

Typically, a superabsorbent polymer has a hydrophilic surface, and thus irreversible agglomeration thereof may occur due to capillary force, hydrogen bonding, inter-particular diffusion, or inter-particular van der Waals force, by water present between the particles upon drying after water absorption. Hence, water is essentially used in the course of polymerization and surface crosslinking of the superabsorbent polymer, and thereby agglomeration is generated, thus increasing internal loads, ultimately incurring damage to the system. Furthermore, since the agglomerated superabsorbent polymer has a large particle size unsuitable for use in applications, a disintegration process has to be implemented so that such a large particle size is decreased properly. Also, strong force is applied in the disintegration process, undesirably deteriorating the properties of the superabsorbent polymer attributed to attrition.

In order to solve such problems, attempts are made to introduce a variety of microparticles that are present on the surface of the superabsorbent polymer and function to prevent direct agglomeration of the polymer particles. In the case where the microparticles are added in an excessive amount, agglomeration may be prevented, but absorption performance of the superabsorbent polymer may decrease.

To solve such problems, the microparticles introduced to the superabsorbent polymer according to the present invention have a particle size ranging from 2 nm to 50 μm. Also, the microparticles have a BET specific surface area of 300~1500 $m^2/g$, preferably 500~1500 $m^2/g$, and more preferably 600~1500 $m^2/g$. Also, the microparticles have superhydrophobicity with a water contact angle of 125° or more, preferably 135° or more, and more preferably 140° or more. Furthermore, the particles (B) may have a particle size ranging from 2 nm to 50 μm and superhydrophobicity with a water contact angle of 125° or more.

The microparticles have a porosity of 50% or more, and preferably 90% or more. Since the superabsorbent polymer having improved anti-caking properties according to the present invention includes the microparticles having the properties as above, the effect of water present on the surface of the polymer may decrease, and also, the use of the microparticles may remarkably reduce agglomeration. Even when a relatively small amount of microparticles is used, permeability may be easily increased, and high water content and maintenance thereof may be readily ensured.

In the method of preparing the superabsorbent polymer according to the present invention, the particles (B) may include any component without limitation so long as it has the above properties, and specific examples thereof may include, but are not limited to, inorganic oxides, such as silica ($SiO_2$), alumina, titania ($TiO_2$), carbon, inorganic compounds, organic polymers, ion exchange resins, metals, metal salts, etc.

Also, adding the microparticles may include, but is not limited to, dispersing microparticles in a monomer solution, adding microparticles to a hydrous gel polymer and then dry mixing them with primarily dried polymer particles, dispersing microparticles in water or an organic solvent having a dissolved surface crosslinking agent upon surface crosslinking, dry mixing microparticles separately from water or an organic solvent having a dissolved surface crosslinking agent upon surface crosslinking, or dry mixing microparticles with a surface crosslinked product.

In the superabsorbent polymer having improved anti-caking properties, the water (C) is contained in an amount of 0.1~20.0 parts by weight, preferably 1.0~10.0 parts by weight, and more preferably 2.5~7.5 parts by weight, based on 100 parts by weight of the superabsorbent polymer (A) and the particles (B). If the amount of the water (C) is less than the lower limit, attrition resistance is not sufficiently obtained. In contrast, if the amount thereof exceeds the upper limit, surface stickiness of the polymer may increase, and irreversible agglomeration of superabsorbent polymer particles may occur, undesirably deteriorating processability of the polymer and changing the particle size thereof, making it difficult to serve as a final product.

In the process of preparing the superabsorbent polymer, water that is a polymerization medium is variously used in a manner that facilitates the dispersion of the crosslinking solution during the surface crosslinking. Also, residual moisture of the final product functions as an anti-static agent and a plasticizer for resin, and plays a role in suppressing the formation of very small superabsorbent polymer dust in the course of applications and also preventing the attrition of the superabsorbent polymer particles. Generally, however, when water is added even in a small amount to the superabsorbent polymer, surface stickiness of the polymer may be increased by the water absorbed to the surface thereof, and irreversible agglomeration of the superabsorbent polymer particles may take place. The increase in stickiness and the agglomeration as mentioned above may result in poor processability, including high loads on the preparation and application processes, consequently increasing the particle size of the superabsorbent polymer and deteriorating the properties and the productivity. Superabsorbent polymers have been studied to date in terms of the polymerization process thereof and enhancements in absorption capacity thereby, and surface crosslinking for increasing the surface properties of the superabsorbent polymer or the absorption under pressure thereof. Furthermore, research is ongoing into changes in the surface properties of superabsorbent polymers to increase permeability or to prevent caking upon storage of superabsorbent polymers (anti-caking).

In the present invention, water is added in the above amount range to the superabsorbent polymer to thereby increase moisture content, so that water functions as a plasticizer, thereby minimizing physical damage to the superabsorbent polymer to satisfy both high moisture content and high processability, ultimately increasing attrition resistance of the superabsorbent polymer. In this procedure, the heated water is used or the temperature of the superabsorbent polymer is raised, and thereby the rate of diffusion of the added water into the superabsorbent polymer may increase, thus shortening the aging time, compared to conventional techniques. Hence, when the superabsorbent polymer is applied to final products such as diapers, deterioration of the properties thereof due to physical attrition by compression or strong air movement during production of the diapers may be minimized.

In the superabsorbent polymer having improved anti-caking properties, the superabsorbent polymer (A) is obtained by a) preparing a hydrous gel polymer from a monomer composition comprising a water-soluble ethylenic unsaturated monomer and a polymerization initiator by thermal polymerization or photopolymerization; b) drying the hydrous gel polymer; c) grinding the dried hydrous gel polymer, thus obtaining superabsorbent polymer particles; and d) adding the superabsorbent polymer particles with a surface crosslinking agent so that a surface crosslinking reaction is carried out.

As used herein, the term "superabsorbent polymer particles" refers to particles obtained by drying and grinding the hydrous gel polymer. More specifically, the hydrous gel polymer is a material in a hard jelly phase with a size of 1 cm or more having water in a large amount (50% or more) after completion of the polymerization. The hydrous gel polymer is dried and ground in a powder phase, yielding superabsorbent polymer particles. Thus, the hydrous gel polymer corresponds to a process intermediate.

In the superabsorbent polymer (A) according to the present invention, a) preparing the hydrous gel polymer from the monomer composition comprising the water-soluble ethylenic unsaturated monomer and the polymerization initiator by thermal polymerization or photopolymerization is performed.

To produce the superabsorbent polymer according to the present invention, a polymer may be prepared by steps and methods typically used in the art. Specifically, upon formation of the superabsorbent polymer according to the present invention, the monomer composition includes a polymerization initiator. Depending on the polymerization method, when photopolymerization is performed, a photopolymerization initiator is used, and when thermal polymerization is performed, a thermal polymerization initiator is employed. Even when the photopolymerization is conducted, a predetermined amount of heat is generated due to irradiation with UV light and also through the polymerization that is an exothermic reaction, and thus a thermal polymerization initiator may be additionally used.

In the method of preparing the superabsorbent polymer according to the present invention, the thermal polymerization initiator is not particularly limited, but preferably includes at least one selected from the group consisting of a persulfate-based initiator, an azo-based initiator, hydrogen peroxide, and ascorbic acid. Specifically, examples of the persulfate-based initiator may include sodium persulfate ($Na_2S_2O_8$), potassium persulfate ($K_2S_2O_8$), and ammonium persulfate (($Na_4)_2S_2O_8$); and examples of the azo-based initiator may include 2,2-azobis(2-amidinopropane)dihydrochloride, 2,2-azobis-(N,N-dimethylene)isobutyramidine dihydrochloride, 2-(carbamoylazo)isobutyronitrile, 2,2-azobis [2-(2-imidazolin-2-yl)propane]dihydrochloride, and 4,4-azobis-(4-cyanovaleric acid).

In the method of preparing the superabsorbent polymer according to the present invention, the photopolymerization initiator is not particularly limited, but preferably includes at least one selected from the group consisting of benzoin ether, dialkyl acetophenone, hydroxyl alkylketone, phenyl glyoxylate, benzyl dimethyl ketal, acyl phosphine, and α-aminoketone. A specific example of the acyl phosphine may include commercially available lucirin TPO, namely, 2,4,6-trimethyl-benzoyl-trimethyl phosphine oxide.

In the method of preparing the superabsorbent polymer according to the present invention, the water-soluble ethylenic unsaturated monomer is not particularly limited so long as it is a monomer typically used to synthesize a superabsorbent polymer, and preferably includes any one or more selected from the group consisting of an anionic monomer and salts thereof, a nonionic hydrophilic monomer, and an amino group-containing unsaturated monomer and quaternary salts thereof. Particularly useful is any one or more selected from the group consisting of anionic monomers and salts thereof, such as acrylic acid, methacrylic acid, maleic anhydride, fumaric acid, crotonic acid, itaconic acid, 2-acryloylethanesulfonic acid, 2-methacryloylethanesulfonic acid, 2-(meth)acryloylpropanesulfonic acid, and 2-(meth)acrylamide-2-methylpropane sulfonic acid; nonionic hydrophilic monomers, such as (meth)acrylamide, N-substituted (meth)acrylate, 2-hydroxyethyl(meth)acrylate, 2-hydroxypropyl (meth)acrylate, methoxypolyethyleneglycol (meth)acrylate, and polyethyleneglycol (meth)acrylate; and amino group-containing unsaturated monomers and quaternary salts thereof, such as (N,N)-dimethylaminoethyl (meth)acrylate, and (N,N)-dimethylaminopropyl (meth)acrylamide. More preferably, acrylic acid or salts thereof are used. When acrylic acid or salts thereof are used as the monomer, a superabsorbent polymer having improved absorbability may be obtained advantageously.

In the method of preparing the superabsorbent polymer according to the present invention, the monomer composition may include a predetermined amount of a polymer or resin powder having a small particle size of less than 150 μm in the prepared superabsorbent polymer powder to exhibit resource recycling effects. Specifically, the polymer or resin powder having a particle size of less than 150 μm may be added before initiation of the polymerization of the monomer composition, or in the early, middle or late step after initiation of the polymerization. As such, the added amount thereof is not limited, but is preferably set to 1~10 parts by weight based on 100 parts by weight of the monomer contained in the monomer composition, in order to prevent the properties of the final superabsorbent polymer from deteriorating.

In the method of preparing the superabsorbent polymer according to the present invention, the concentration of the water-soluble ethylenic unsaturated monomer of the monomer composition may be appropriately determined in consideration of the polymerization time and the reaction conditions, and is preferably set to 40~55 wt %. If the concentration of the water-soluble ethylenic unsaturated monomer is less than 40 wt %, economic benefits are negated. In contrast, if the concentration thereof exceeds 55 wt %, grinding efficiency of the hydrous gel polymer may decrease.

Preparing the hydrous gel polymer from the monomer composition by thermal polymerization or photopolymerization is not limited so long as it is typically useful. Specifically, the polymerization method is largely classified into thermal polymerization and photopolymerization depending on the polymerization energy source. Typically, thermal polymerization is conducted using a reactor with a stirring shaft, such as a kneader, and photopolymerization is implemented using a reactor with a movable conveyor belt. However, the above polymerization method is merely illustrative, and the present invention is not limited to such a polymerization method.

For example, hot air is fed to a reactor with a stirring shaft, such as a kneader, or the reactor is heated, so that thermal polymerization is carried out, yielding a hydrous gel polymer, which is then discharged to a size ranging from ones of mm to ones of cm through the outlet of the reactor depending on the shape of the stirring shaft of the reactor. Specifically, the size of the hydrous gel polymer may vary depending on the concentration of the supplied monomer composition and the supply rate thereof, and typically a hydrous gel polymer having a particle size of 2~50 mm may be obtained.

Also, when photopolymerization is carried out using a reactor with a movable conveyor belt, a hydrous gel polymer in a sheet form with a belt width may result. As such, the thickness of the polymer sheet may vary depending on the concentration of the supplied monomer composition and the supply rate thereof, but the monomer composition is preferably supplied so as to obtain a polymer sheet having a thickness of 0.5~5 cm. In the case where the monomer composition is supplied to the extent that a very thin polymer sheet is formed, production efficiency may decrease undesirably. If the thickness of the polymer sheet is greater than 5 cm, polymerization may not be uniformly carried out throughout the sheet that is too thick.

The light source usable for photopolymerization is not particularly limited, and any UV light source may be used without limitation so long as it is known to cause a photopolymerization reaction. For example, light having a wavelength of about 200~400 nm may be used, and a UV light source such as a Xe lamp, an Hg lamp, or a metal halide lamp may be adopted. Furthermore, photopolymerization may be conducted at an intensity ranging from about 0.1 mw/cm$^2$ to about 1 kw/cm$^2$ for a period of time ranging from about 5 sec to about 10 min. If the intensity of light applied to the photopolymerization reaction and the time thereof are excessively small and short, polymerization may not sufficiently occur. In contrast, if they are excessively large and long, the quality of the superabsorbent polymer may deteriorate.

Next, b) drying the hydrous gel polymer is performed.

The hydrous gel polymer obtained in a) typically has a moisture content of 30~60 wt %. As used herein, the term "moisture content" refers to an amount of moisture based on the total weight of the hydrous gel polymer, namely, a value obtained by subtracting the weight of the dried polymer from the weight of the hydrous gel polymer (Specifically, it is defined as a value calculated by measuring a weight reduction due to moisture evaporation from the polymer during drying the polymer at high temperature via IR heating. As such, the drying is performed in such a manner that the temperature is increased from room temperature to 180° C. and then maintained at 180° C., and the total drying time is set to 20 min including 5 min necessary for increasing the temperature).

The hydrous gel polymer obtained in a) is dried, and preferably the drying temperature is set to 150~250° C. As used herein, the term "drying temperature" refers to a temperature of a heat medium supplied for the drying process or a temperature of a drying reactor including a heat medium and a polymer in the drying process.

If the drying temperature is lower than 150° C., the drying time may become excessively long, and the properties of the final superabsorbent polymer may thus deteriorate. In contrast, if the drying temperature is higher than 250° C., only the surface of the polymer may be excessively dried, and thereby fine powder may be generated in the subsequent grinding process, and the properties of the final superabsorbent polymer may deteriorate. The drying is preferably performed at a temperature of 150~250° C., and more preferably 160~200° C.

The drying time is not limited, but may be set to 20~90 min taking into account the process efficiency.

Also, the drying process is not limited so long as it is typically used to dry the hydrous gel polymer. Specific examples thereof may include hot air supply, IR irradiation, microwave irradiation, and UV irradiation. The polymer after the drying process may have a moisture content of 0.1~10 wt %.

Meanwhile, the method of preparing the superabsorbent polymer according to the present invention may further comprise a simple grinding process before the drying process, as necessary, in order to increase the drying efficiency. The simple grinding process before the drying process is conducted so that the particle size of the hydrous gel polymer is 1~15 mm. Grinding the particle size of the polymer to less than 1 mm is technically difficult due to high moisture content of the hydrous gel polymer, and the ground particles may agglomerate. On the other hand, if the polymer is ground to a particle size of greater than 15 mm, an effect of increasing the drying efficiency via the grinding process may become insignificant.

In the simple grinding process before the drying process, any grinder may be used without limitation. A specific example thereof may include, but is not limited to, any one selected from the group consisting of a vertical pulverizer, a turbo cutter, a turbo grinder, a rotary cutter mill, a cutter mill, a disc mill, a shred crusher, a crusher, a chopper, and a disc cutter.

When the grinding process is performed to increase the drying efficiency before the drying process in this way, the polymer having high moisture content may stick to the surface of the grinder. Thus, in order to increase the grinding efficiency of the hydrous gel polymer before the drying process, an additive able to prevent stickiness upon grinding may be further used. Specifically, the kind of usable additive is not limited. Examples thereof may include, but are not limited to, a powder agglomeration inhibitor, such as steam, water, a surfactant, and inorganic powder such as clay or silica; a thermal polymerization initiator, such as a persulfate-based initiator, an azo-based initiator, hydrogen peroxide, and ascorbic acid; and a crosslinking agent, such as an epoxy-based crosslinking agent, a diol-based crosslinking agent, a bifunctional or trifunctional or higher polyfunctional acrylate, and a monofunctional compound having a hydroxyl group.

In the method of preparing the superabsorbent polymer according to the present invention, c) grinding the dried hydrous gel polymer is performed to obtain superabsorbent polymer particles, after the drying process. The superabsorbent polymer particles resulting from the grinding process have a particle size of 150~850 µm. In the method of preparing the superabsorbent polymer according to the present invention, a grinder used to obtain such a particle size may include, but is not limited to, a pin mill, a hammer mill, a screw mill, a roll mill, a disc mill, or a jog mill.

In d), the superabsorbent polymer particles are added with a surface crosslinking agent so that surface crosslinking is carried out. As such, the same or different surface crosslinking agent may be added depending on the particle size of the superabsorbent polymer particles.

In the method of preparing the superabsorbent polymer according to the present invention, the surface crosslinking agent is not limited so long as it is able to react with the functional group of the polymer. In order to improve the properties of the superabsorbent polymer, the surface crosslinking agent may include at least one selected from the group consisting of a polyhydric alcohol compound; an epoxy compound; a polyamine compound; a haloepoxy compound; a haloepoxy compound condensed product; an oxazoline compound; a mono-, di- or poly-oxazolidinone compound; a cyclic urea compound; a polyhydric metal salt; and an alkylene carbonate compound.

Specifically, the polyhydric alcohol compound may include at least one selected from the group consisting of mono-, di-, tri-, tetra- or poly-ethylene glycol, monopropylene glycol, 1,3-propanediol, dipropylene glycol, 2,3,4-trimethyl-1,3-pentanediol, polypropylene glycol, glycerol, polyglycerol, 2-butene-1,4-diol, 1,4-butanediol, 1,3-butanediol, 1,5-pentanediol, 1,6-hexanediol, and 1,2-cyclohexanedimethanol.

Examples of the epoxy compound may include ethylene glycol diglycidyl ether and glycidol, and the polyamine compound may include at least one selected from the group consisting of ethylene diamine, diethylene triamine, triethylene tetramine, tetraethylene pentamine, pentaethylene hexamine, polyethyleneimine, and polyamide polyamine.

Examples of the haloepoxy compound may include epichlorohydrine, epibromohydrine, and α-methylepichlorohydrine. The mono-, di- or poly-oxazolidinone compound may be exemplified by 2-oxazolidinone. The alkylene carbonate compound may include ethylene carbonate. These compounds may be used alone or in combination. To increase the efficiency of the surface crosslinking process, the surface crosslinking agent preferably includes at least one polyhydric alcohol compound, and more preferably includes a polyhydric alcohol compound having 2 to 10 carbon atoms.

The amount of the surface crosslinking agent added to treat the surface of the polymer particles may be properly determined depending on the kind of surface crosslinking agent or the reaction conditions, and is set to 0.001~5 parts by weight, preferably 0.01~3 parts by weight, and more preferably 0.05~2 parts by weight, based on 100 parts by weight of the ground superabsorbent polymer particles.

If the amount of the surface crosslinking agent is too small, a surface crosslinking reaction seldom occurs. In contrast, if the amount thereof exceeds 5 parts by weight based on 100 parts by weight of the polymer, properties of the superabsorbent polymer may deteriorate due to an excessive surface crosslinking reaction.

As such, adding the surface crosslinking agent to the polymer is not limited. The surface crosslinking agent and the polymer powder may be placed in a reaction bath and mixed, or spraying the surface crosslinking agent onto the polymer powder or continuously supplying the polymer and the crosslinking agent to a reaction bath such as a mixer that continuously operates may be implemented.

Upon adding the surface crosslinking agent, the surface temperature of the polymer is preferably 60~90° C.

In an embodiment of the present invention, the temperature of the polymer itself may be 20~80° C. upon adding the surface crosslinking agent, so that increasing the temperature to a reaction temperature is carried out within 1~60 min to perform surface crosslinking in the presence of the surface crosslinking agent. To show the temperature of the polymer itself as above, processes after the drying process that is carried out at relatively high temperature are continuously performed, and the process time may be shortened. Alternatively, the polymer may be separately heated when it is difficult to shorten the process time.

In the method of preparing the superabsorbent polymer according to the present invention, the surface crosslinking agent added to the polymer may be heated, so that increasing the temperature to a reaction temperature is carried out within 1~60 min to perform surface crosslinking in the presence of the surface crosslinking agent.

Meanwhile, in the method of preparing the superabsorbent polymer according to the present invention, when the surface crosslinking reaction is carried out after increasing the temperature to a reaction temperature within 1~60 min so as to be adapted for surface crosslinking, the efficiency of the surface crosslinking process may be improved. Ultimately, the residual monomer content of the final superabsorbent polymer may be minimized, and the superabsorbent polymer having superior properties may be attained. As such, the temperature of the added surface crosslinking agent is adjusted to 5~60° C., and preferably 10~40° C. If the temperature of the surface crosslinking agent is lower than 5° C., an effect of decreasing the heating rate to the surface crosslinking reaction via heating of the surface crosslinking agent may become insignificant. In contrast, if the temperature of the surface crosslinking agent is higher than 60° C., the surface crosslinking agent may not be uniformly dispersed in the polymer. As used herein, the temperature of the surface crosslinking reaction may be defined as a total temperature of both the polymer and the surface crosslinking agent added for the crosslinking reaction.

A heating member for the surface crosslinking reaction is not limited. Specifically, a heat medium may be supplied, or direct heating may be conducted using electricity, but the present invention is not limited thereto. Specific examples of the heat source may include steam, electricity, UV light, and IR light. Additionally, a heated thermal fluid may be used.

In the method of preparing the superabsorbent polymer according to the present invention, after heating for the crosslinking reaction, the crosslinking reaction is carried out for 1~60 min, preferably 5~40 min, and more preferably 10~20 min. If the crosslinking reaction time is shorter than 1 min, the crosslinking reaction may not sufficiently occur. In contrast, if the crosslinking reaction time is longer than 60 min, properties of the superabsorbent polymer may deteriorate due to the excessive surface crosslinking reaction, and the polymer may be subjected to attrition due to long-term residence in the reactor.

The superabsorbent polymer having improved anti-caking properties thus obtained may have a moisture content of 0.1 wt % or more.

In addition, the present invention addresses a method of preparing the superabsorbent polymer having improved anti-caking properties, comprising: a) adding a superabsorbent polymer (A) with 0.0001~15.0 parts by weight of particles (B) having i) a BET specific surface area of 300~1500 $m^2/g$ and ii) a porosity of 50% or more, based on 100 parts by weight of the superabsorbent polymer (A); and b) adding the superabsorbent polymer (A) and the particles (B) obtained in a) with 0.1~20.0 parts by weight of water (C), based on 100 parts by weight of the superabsorbent polymer (A) and the particles (B), and performing at least one of heating treatment and aging time control treatment, yielding the superabsorbent polymer having improved anti-caking properties.

More specifically, the heating treatment in b) may be conducted by heating, to 26~95° C., at least one selected from the group consisting of the superabsorbent polymer (A) and the particles (B); a stirrer; and water, and the temperature of the superabsorbent polymer and the microparticles, water, or the stirrer for use in stirring upon aging, may be adjusted. Given the above heating treatment range, caking of the particles after addition of water to the superabsorbent polymer may be decreased and thus the aging time may be reduced, compared to at a temperature of 15~25° C. This means that the process time is shortened and the preparation process may be simplified. If the heating temperature is lower than the lower limit, an effect of reducing the aging time cannot be obtained. In contrast, if the heating temperature is higher than the upper limit, the rate of absorption of the superabsorbent polymer may increase, thus evaporating water or making it difficult to attain uniform moisture content.

In an embodiment of the present invention, the temperature of the superabsorbent polymer (SAP) passed through a cooler and a separator after surface crosslinking during the production process of the superabsorbent polymer amounts to 60~70° C. As such, when water is immediately added without the need for additionally raising the temperature of the superabsorbent polymer, the aforementioned effect may be exhibited, thus obviating the additional use of energy.

Also, the aging time control treatment in b) is conducted by adding the superabsorbent polymer (A) and the particles (B) with water (C) at 15~25° C. and then aging the resulting mixture with stirring at 5~1500 rpm at 26~95° C. for 1~120 min Given the above aging treatment range, no caking occurs in the procedures from addition of the superabsorbent polymer with water to packaging thereof.

Even when caking does not occur upon addition of the superabsorbent polymer with water, it may be caused under continuous loads for a long period of time, but prevention thereof is possible. If the aging time is shorter than the lower limit, caking of the particles may take place. In contrast, if the aging time is longer than the upper limit, economic benefits are negated due to unnecessary processing.

Also, the heating treatment and the aging time control treatment in b) are implemented in such a manner that at least one selected from the group consisting of the superabsorbent polymer (A) and the particles (B); the stirrer; and water is heated to 26~95° C., and then aged with stirring at 5~1500 rpm at 15~25° C. for 1~120 min. As such, there are no significant changes in properties such as particle size distribution, flowability and bulk density depending on the aging time. This means that addition of water to the superabsorbent polymer at raised temperature results in remarkably decreased aging time, compared to addition of water at room temperature.

Whereas, even when water is added to the superabsorbent polymer at 15~25° C. corresponding to room temperature, caking may not occur under the condition that the aging time is increased. However, an increase in the aging time may undesirably result in lowered productivity.

In the method of preparing the superabsorbent polymer having improved anti-caking properties, the particles (B) having the properties of i) and ii) are preferably added in an amount of 0.0001~15.0 parts by weight, more preferably 0.001~2.0 parts by weight, and still more preferably 0.05~0.15 parts by weight, based on 100 parts by weight of the superabsorbent polymer (A). If the amount of the particles (B) is less than the lower limit, desired effects fail to be obtained. In contrast, if the amount thereof exceeds the upper limit, economic benefits may be negated due to the excessive use of the particles (B).

Typically, a superabsorbent polymer has a hydrophilic surface, and thus irreversible agglomeration thereof may occur due to capillary force, hydrogen bonding, inter-particular diffusion, or inter-particular van der Waals force, by water present between the particles upon drying after water absorption. Hence, water is essentially used in the course of polymerization and surface crosslinking of the superabsorbent polymer, and thereby agglomeration is generated, thus increasing internal loads, ultimately incurring damage to the system. Furthermore, since the agglomerated superabsorbent polymer has a large particle size unsuitable for use in applications, a disintegration process has to be implemented so that such a large particle size is decreased properly. Also, strong force is applied in the disintegration process, undesirably deteriorating the properties of the superabsorbent polymer attributed to attrition.

In order to solve such problems, attempts are made to introduce a variety of microparticles that are present on the surface of the superabsorbent polymer and function to prevent direct agglomeration of the polymer particles. In the case where the microparticles are added in an excessive amount, agglomeration may be prevented, but absorption performance of the superabsorbent polymer may decrease.

To solve such problems, the microparticles introduced to the superabsorbent polymer according to the present invention have a particle size ranging from 2 nm to 50 μm. Also, the microparticles have a BET specific surface area of 300~1500 $m^2/g$, preferably 500~1500 $m^2/g$, and more preferably 600~1500 $m^2/g$. The microparticles have superhydrophobicity with a water contact angle of 125° or more, preferably 135° or more, and more preferably 140° or more. Furthermore, the particles (B) may have a particle size ranging from 2 nm to 50 μm and superhydrophobicity with a water contact angle of 125° or more.

The microparticles have a porosity of 50% or more, and preferably 90% or more. Since the microparticles having the properties as above are used in the superabsorbent polymer having improved anti-caking properties according to the present invention, the effect of water present on the surface of the polymer may decrease, and also, the use of porous superhydrophobic microparticles may remarkably reduce the agglomeration. Even when a relatively small amount of microparticles is used, permeability may be easily increased, and high water content and maintenance thereof may be readily ensured.

In the method of preparing the superabsorbent polymer according to the present invention, the particles (B) may include any component without limitation so long as it has the above properties, and examples thereof may include, but are not limited to, inorganic oxides, such as silica ($SiO_2$), alumina, titania ($TiO_2$), carbon, inorganic compounds, organic polymers, ion exchange resins, metals, metal salts, etc.

Also, adding the microparticles may include, but is not limited to, dispersing microparticles in a monomer solution, adding microparticles to a hydrous gel polymer and then dry mixing them with primarily dried polymer particles, dispersing microparticles in water or an organic solvent having a dissolved surface crosslinking agent upon surface crosslinking, dry mixing microparticles separately from water or an organic solvent having a dissolved surface crosslinking agent upon surface crosslinking, or dry mixing microparticles with a surface crosslinked product.

In the superabsorbent polymer having improved anti-caking properties, the water (C) is added in an amount of 0.1~20.0 parts by weight, preferably 1.0~10.0 parts by weight, and more preferably 2.5~7.5 parts by weight, based on 100 parts by weight of the superabsorbent polymer (A) and the particles (B). If the amount of the water (C) is less than the lower limit, sufficient attrition resistance cannot be obtained. In contrast, if the amount thereof exceeds the upper limit, surface stickiness of the polymer may increase, and irreversible agglomeration of the superabsorbent polymer particles may occur, undesirably deteriorating processability of the polymer and changing the particle size thereof, making it difficult to serve as a final product.

In the preparation process of the superabsorbent polymer, water that is a polymerization medium is variously used in a manner that facilitates the dispersion of the crosslinking solution during the surface crosslinking. Also, residual moisture of the final product functions as an anti-static agent and a plasticizer for resin, and plays a role in suppressing the formation of very small superabsorbent polymer dust in the course of applications and also preventing the attrition of the superabsorbent polymer particles. Generally, however, when water is added even in a small amount to the superabsorbent polymer, surface stickiness of the polymer may be increased by the water absorbed to the surface thereof, and irreversible agglomeration of the superabsorbent polymer particles may occur. The increase in stickiness and the agglomeration as above may result in poor processability, including high loads on the preparation and application processes, consequently increasing the particle size of the superabsorbent polymer, and deteriorating the properties and the productivity. Such superabsorbent polymers have been studied to date in terms of the polymerization process and improvement in absorption capacity thereby, and surface crosslinking for increasing the surface properties of the superabsorbent polymer or the absorption under pressure thereof. Furthermore, research is carried out into changes in the surface properties of superabsorbent polymers to increase permeability or to prevent caking upon storage of superabsorbent polymers (anti-caking).

In the present invention, water is added in the above amount range to the superabsorbent polymer to thereby increase moisture content, so that water functions as a plasticizer, thereby minimizing physical damage to the superabsorbent polymer to satisfy both high moisture content and high processability, ultimately increasing attrition resistance of the superabsorbent polymer. In this procedure, the heated water is used or the temperature of the superabsorbent polymer is raised, and thereby the rate of diffusion of the added water into the superabsorbent polymer may increase, thus shortening the aging time, compared to conventional techniques. Hence, when the superabsorbent polymer is applied to final products such as diapers, deterioration of the properties thereof due to physical attrition by compression or strong air movement during production of the diapers may be minimized.

In an embodiment of the present invention, the preparation method may further comprise c) checking anti-caking properties of the superabsorbent polymer through caking testing, after b). This caking testing may be carried out for 1 min to 50 hr or for ones of months, under a load of 2.66 psi.

The superabsorbent polymer having improved anti-caking properties, as obtained by the above preparation method, has a moisture content of 0.1 wt % or more.

In the method of preparing the superabsorbent polymer having improved anti-caking properties, the superabsorbent polymer (A) is obtained by a) preparing a hydrous gel polymer from a monomer composition comprising a water-soluble ethylenic unsaturated monomer and a polymerization initiator by thermal polymerization or photopolymerization; b) drying the hydrous gel polymer; c) grinding the dried hydrous gel polymer, thus obtaining superabsorbent polymer particles; and d) adding the superabsorbent polymer particles with a surface crosslinking agent so that a surface crosslinking reaction is carried out.

The water-soluble ethylenic unsaturated monomer may include any one or more selected from the group consisting of an anionic monomer and salts thereof, a nonionic hydrophilic monomer, and an amino group-containing unsaturated monomer and quaternary salts thereof. The polymerization initiator for thermal polymerization may include any one or more selected from the group consisting of a persulfate-based initiator, an azo-based initiator, hydrogen peroxide, and ascorbic acid, and the polymerization initiator for photopolymerization may include any one or more selected from the group consisting of benzoin ether, dialkyl acetophenone, hydroxyl alkylketone, phenyl glyoxylate, benzyl dimethyl ketal, acyl phosphine, and α-aminoketone.

The drying process in b) is performed at 150~250° C., and the superabsorbent polymer particles obtained after the grinding process in c) may have a particle size of 150~850 μm.

The surface crosslinking agent may include any one or more selected from the group consisting of a polyhydric alcohol compound; an epoxy compound; a polyamine compound; a haloepoxy compound; a haloepoxy compound condensed product; an oxazoline compound; a mono-, di- or poly-oxazolidinone compound; a cyclic urea compound; a polyhydric metal salt; and an alkylene carbonate compound.

In addition thereto, a detailed description of the superabsorbent polymer (A), the particles (B), and the water (C) in the method of preparing the superabsorbent polymer having improved anti-caking properties according to the present invention quotes the description of the superabsorbent polymer having improved anti-caking properties herein.

A better understanding of the present invention may be obtained via the following examples that are set forth to illustrate, but are not to be construed as limiting the scope of the present invention. The scope of the present invention is shown in the claims, and also contains all modifications within the meaning and range equivalent to the claims. Unless otherwise mentioned, "%" and "part" showing the amount in the following examples and comparative examples refer to a mass basis.

PREPARATION EXAMPLE

Preparation of Hydrous Gel Polymer and Superabsorbent Polymer 100 g of acrylic acid, 0.3 g of polyethyleneglycol diacrylate as a crosslinking agent, 0.033 g of diphenyl(2,4,6-trimethylbenzoyl)-phosphine oxide as an initiator, 38.9 g of sodium hydroxide (NaOH), and 103.9 g of water were mixed, thus preparing a monomer mixture. The monomer mixture was then placed on a continuously moving conveyor belt, and irradiated with UV light (at 2 mW/cm$^2$) so that UV polymerization was carried out for 2 min, thus obtaining a hydrous gel polymer. The hydrous gel polymer thus obtained was cut to a size of 5×5 min, dried in a hot air oven at 170° C. for 2 hr, and ground using a pin mill, and then sorted using a sieve, thereby obtaining a superabsorbent polymer having a particle size of 150~850 μm. As a surface crosslinking agent, a liquid mixture comprising 0.75 g of ethylene carbonate and 6.75 g of water was added and mixed for 60 sec. The resulting mixture was reacted at 190° C. for 60 min, thus obtaining a non-ground superabsorbent polymer. Also, the particle size of the non-ground superabsorbent polymer before grinding was measured, and such a polymer was ground using a pin mill and sorted using a sieve, thereby obtaining a superabsorbent polymer having a particle size of 150~850 μm.

As porous superhydrophobic microparticles, an aerogel (available from JIOS) was used, and had an average particle size of 5 μm, a BET specific surface area of 720 m$^2$/g, a water contact angle of 144°, and a porosity of 95%.

The particle size of the Aerogel was measured through Laser Diffraction using HELOS (Helium-Neon Laser Optical System) based on ISO 13320. The specific surface area thereof was measured using a BET meter (Micromeritics 3Flex). The porosity thereof was determined from the tap density ($\rho_t$) and the true density ($\rho_s$) of Equation 1 below.

$$\text{Porosity (\%)} = (1 - \rho_t/\rho_s) \ast 100 \quad \text{[Equation 1]}$$

In order to measure the true density, a pycnometer (Accupyc II 1340) was used, and the tap density was measured using a volumeter (Engelsmann Model STAV II).

The water contact angle was measured using a contact angle analyzer (KRUSS DSA100), and was specifically determined in a manner in which double-sided tape was attached to a flat glass plate, microparticles were applied in a monolayer thereon, and then 5 μL of ultrapure water was placed in the form of drop on the monolayer, and the angle between the water drop and the glass plate was measured four times and averaged.

The porous superhydrophobic microparticles in an amount of 600 ppm based on the amount of the superabsorbent polymer were placed in a stirrer, and during stirring, water was added in amounts of 0 (P/D), 2.5, 5.0, and 7.5 wt %, based on the amount of the superabsorbent polymer. Also, the porous superhydrophobic microparticles in amounts of 600 ppm and 1000 ppm based on the amount of the superabsorbent polymer were placed in a stirrer, and during stirring, water was added in amounts of 0, 2.5, and 5.0 wt % based on the amount of the superabsorbent polymer.

EXAMPLE 1

Preparation of Superabsorbent Polymer having Improved Anti-caking Properties 1 (Temperature Control)

In order to evaluate anti-caking of particles a long period of time after addition of water to a superabsorbent polymer, testing was carried out in such a manner that water was added under the condition that the temperature of a superabsorbent polymer was raised. Specifically, a superabsorbent polymer treated with 600 ppm of an aerogel as porous superabsorbent microparticles was placed in an oven and adjusted to about 60° C., after which the superabsorbent polymer was placed in a stirrer maintained at 70° C. and then added with 2.5 wt % of water. Subsequently, 100 g of the sample was taken and then underwent a load of 2.66 psi for 1 hr, after which caking of the superabsorbent polymer was checked.

Figure 1A:
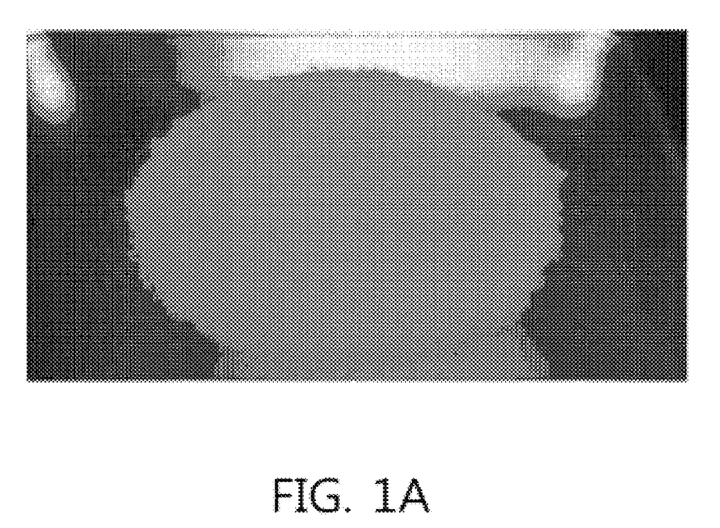
FIGS. 1A and 1B illustrate the test results upon addition of water at raised temperature and upon addition of water at room temperature, respectively, to compare a difference in caking of superabsorbent polymer particles depending on the temperature, in a superabsorbent polymer having improved anti-caking properties according to the present invention.
Figure 1B:
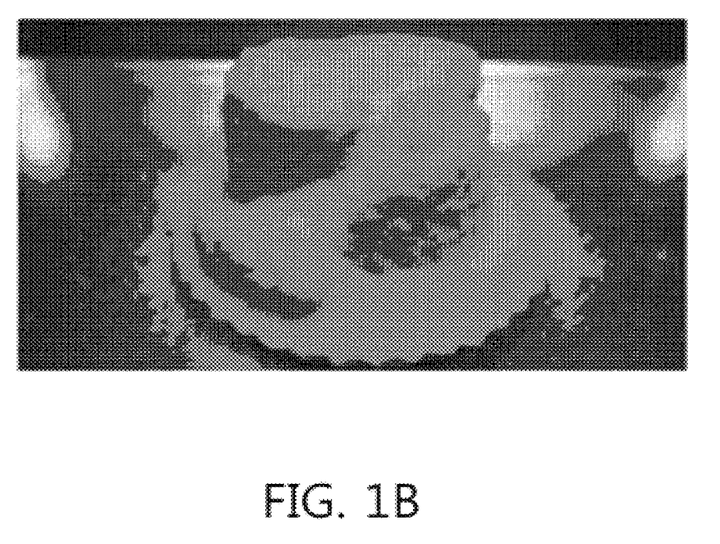
Figure 2A:
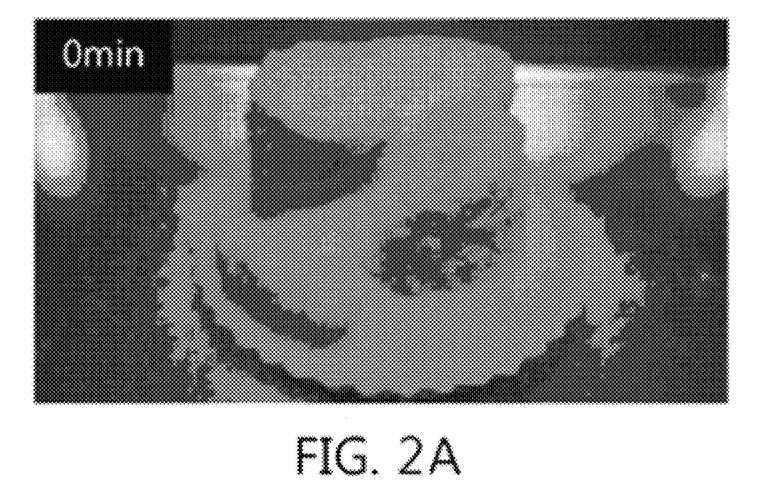
FIGS. 2A and 2B illustrate the results of caking testing (0 min) without aging, to evaluate the extent of caking depending on the aging time after addition of water under conditions of room temperature, in a superabsorbent polymer having improved anti-caking properties according to the present invention.
Figure 2B:
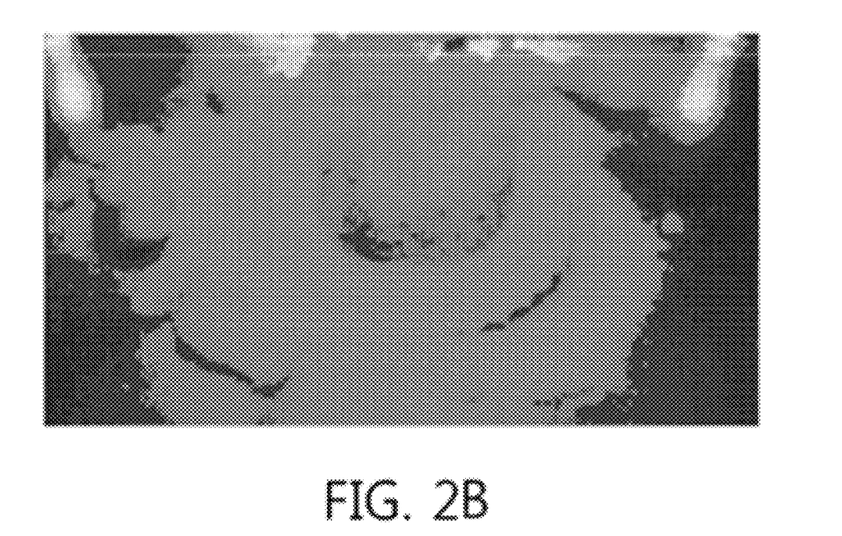
Figure 3A:
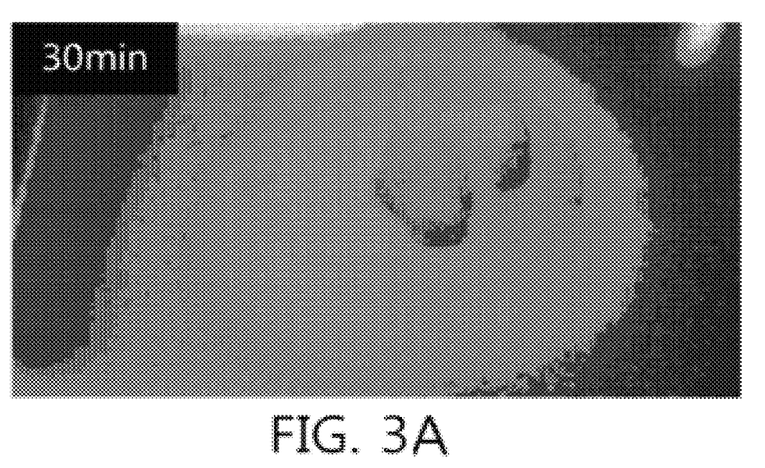
FIGS. 3A and 3B illustrate the results of aging for 30 min, to evaluate the extent of caking depending on the aging time after addition of water under conditions of room temperature, in a superabsorbent polymer having improved anti-caking properties according to the present invention.
Figure 3B:
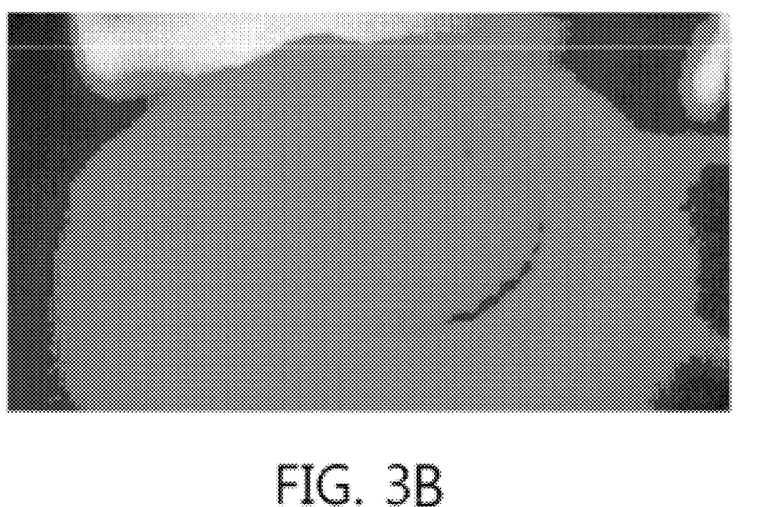

To compare a difference in caking of the superabsorbent polymer particles at different temperatures, the temperature of the superabsorbent polymer and the temperature of the stirrer were set to room temperature under the testing conditions as above, and testing was implemented. Consequently, caking of the particles did not take place as shown in FIG. 1A when water was added under the condition that the temperature of the superabsorbent polymer was raised, but caking of the particles under a load of 2.66 psi occurred seriously as shown in FIG. 1B when water was added at room temperature.

EXAMPLE 2

Preparation of Superabsorbent Polymer having Improved Anti-caking Properties 2 (Aging Time Control)

In order to evaluate anti-caking of particles a long period of time after addition of water to a superabsorbent polymer, testing was carried out in such a manner that water was added under the condition that a superabsorbent polymer was at room temperature, followed by aging for a predetermined aging time. Specifically, a superabsorbent polymer treated with 600 ppm of an aerogel as porous superabsorbent microparticles was added with 2.5 wt % of water, and then aged for an aging time of 30 min using a stirrer such as a kitchen-aid at room temperature. The sample not subjected to aging was used as control of Example 2. Consequently, as is apparent from FIG. 2 where caking testing was immediately performed (0 min) without aging, caking of the superabsorbent polymer particles was seriously caused, and such caking was maintained even by finger touch. Whereas, as is apparent from FIG. 3 where aging was conducted (30 min) under the same conditions, caking of the particles was significantly reduced and such caking was easily broken by slight finger touch.

EXAMPLE 3

Preparation of Superabsorbent Polymer having Improved Anti-caking Properties 3 (Temperature and Aging Time Control)

Figure 4:
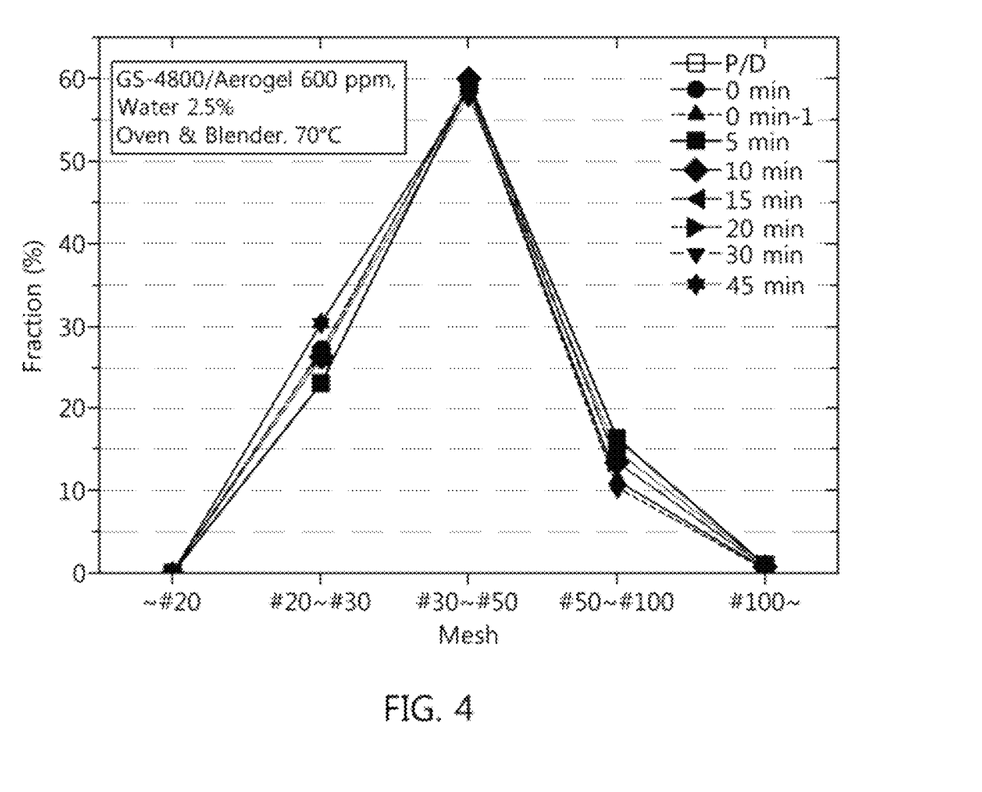
FIG. 4 is a graph illustrating the particle size distribution of the superabsorbent polymer having improved anti-caking properties according to the present invention, depending on the aging time.

In order to evaluate anti-caking of particles a long period of time after addition of water to a superabsorbent polymer, testing was carried out in such a manner that water was added under the condition that the temperature of a superabsorbent polymer was raised. A superabsorbent polymer treated with 600 ppm of an aerogel as porous superabsorbent microparticles was placed in an oven and adjusted to about 60° C., after which the superabsorbent polymer was placed in a stirrer maintained at 70° C. and then added with 2.5 wt % of water. Subsequently, aging was performed for an aging time of 0~45 min using a simple stirrer such as a kitchen-aid at room temperature. Based on the analytical results, the particle size distribution depending on the aging time is illustrated in FIG. 4, and flowability and bulk density depending on the aging time are shown in Table 1 below. As is apparent from the results of FIG. 4 and Table 1, there were no significant changes in the particle size distribution, flowability, and bulk density depending on the aging time. Compared to when water was added at room temperature as in Example 2, when water was added at raised temperature of the superabsorbent polymer under the same conditions, the aging time necessary for reducing caking of the particles was remarkably decreased.

TABLE 1

| Aging time | Flowability (sec) | Bulk density (g/mL) |
|---|---|---|
| GS-4800 P/D | 9.6 | 0.67 |
| 0 min | 10.3 | 0.66 |
| 0 min-1 | 10.1 | 0.67 |
| 5 min | 9.9 | 0.67 |
| 10 min | 10.1 | 0.67 |
| 15 min | 10.2 | 0.67 |
| 20 min | 10.3 | 0.67 |
| 30 min | 10.4 | 0.66 |
| 45 min | 10.2 | 0.67 |

EXAMPLE 4

Preparation of Superabsorbent Polymer having Improved Anti-caking Properties 4 (Temperature Control of Water)

Figure 5:
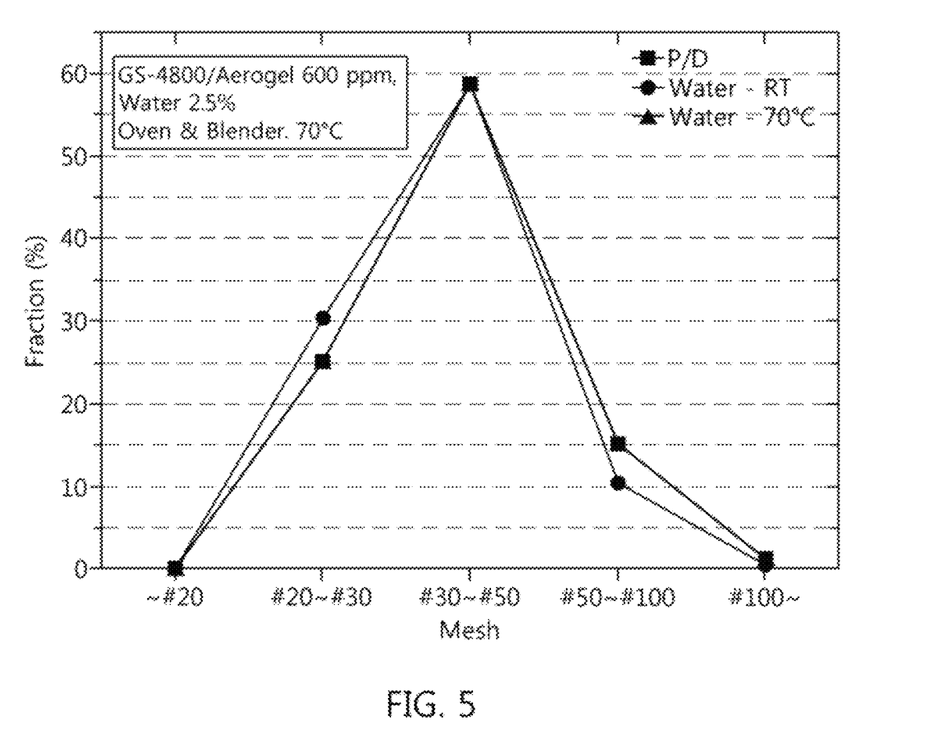
FIG. 5 is a graph illustrating the particle size distribution of the superabsorbent polymer having improved anti-caking properties according to the present invention, depending on the temperature of added water.

Testing was carried out by raising only the temperature of added water under the same conditions as in Example 1. When comparing the results of particle size distribution after addition of water at room temperature and water heated to 70° C., as illustrated in FIG. 5, the same particle size distribution as that of the original superabsorbent polymer (PD) was represented when heated water was added. Thereby, an increase in the temperature of water led to anti-caking of the particles.

EXAMPLE 5

Preparation of Superabsorbent Polymer having Improved Anti-caking Properties 5 (Temperature and Aging Time Control)

Pilot testing was conducted based on lab scale. A superabsorbent polymer treated with 600 ppm of an aerogel as porous superabsorbent microparticles was adjusted to about 60° C., placed in a continuous stirrer at a rate of 40 kg/h, and introduced with 2.5 wt % of water. Then, aging was implemented for 0~50 min using a stirrer at room temperature and the extent of caking of the particles was checked. As in lab testing results, caking did not occur at all of 0, 5, 10, 20, 30, 40, and 50 min Even when the caking time was increased from 1 hr to 48 hr or more, the particles were not caked.

EXAMPLE 6

Preparation of Superabsorbent Polymer having Improved Anti-caking Properties 6 (Aging Temperature and Time Control)

A superabsorbent polymer treated with 600 ppm of an aerogel as porous superabsorbent microparticles was placed in a continuous stirrer at a rate of 40 kg/h at room temperature, and then added with 2.5 wt % of water. Then, aging was implemented for 0~50 min using a stirrer at 50° C., and the extent of caking of the particles was checked. As in the testing results of Example 5, caking did not occur at all of 0, 5, 10, 20, 30, 40, and 50 min.

Also, when the caking time was increased from 1 hr to 48 hr or more, the particles were not caked.

Therefore, according to the present invention, the temperature when adding the superabsorbent polymer with water or the aging time can be controlled, thus preventing caking of superabsorbent polymer particles. Through such factor control, caking of the particles of the superabsorbent polymer can be expected to be blocked during storage or transport of final products after addition of water to the superabsorbent polymer.

What is claimed is:

1. A method of preparing a superabsorbent polymer having improved anti-caking properties, comprising:
    adding water to a superabsorbent polymer and particles to form a composition comprising the superabsorbent polymer, the particles, and the water, wherein a water content of the composition is 0.1-5.0 parts by weight, based on 100 parts by weight of the superabsorbent polymer and the particles; and
    performing an aging time control treatment on the composition to prepare a superabsorbent polymer having improved anti-caking properties,
    wherein the particles are present in an amount of 0.0001-15.0 parts by weight, based on 100 parts by weight of the superabsorbent polymer, wherein the particles have a BET specific surface area of 300-1500 $m^2/g$ and a porosity of 50% or more.

2. The method of claim 1, further comprising: heating at least one of the superabsorbent polymer, particles, or water to a temperature ranging from 26° C. to 95° C.

3. The method of claim 1, wherein the water is added to the composition at a temperature ranging from 15° C. to 25° C., and the aging time control treatment further comprises stirring the composition at 5 rpm to 1500 rpm at a temperature ranging from 26° C. to 95° C. for a time period ranging from 1 min to 120 min.

4. The method of claim 1, further comprising:
    performing a heating treatment followed by the aging time control treatment,
    wherein the heating treatment followed by the aging time control treatment comprises:
    heating at least one of the superabsorbent polymer, the particles, or the water to a temperature ranging from 26° C. to 95° C.;
    then adding the water to the superabsorbent polymer and the particles to form the composition; and
    then stirring the composition at 5 rpm to 1500 rpm at a temperature ranging from 15° C. to 25° C. for a time period ranging from 1 min to 120 min.

5. The method of claim 1, wherein the particles are present in an amount of 0.001-2.0 parts by weight based on 100 parts by weight of the superabsorbent polymer.

6. The method of claim 1, wherein the water content is 2.5-5.0 parts by weight, based on 100 parts by weight of the superabsorbent polymer and the particles.

7. The method of claim 1, wherein the particles have a particle size ranging from 2 nm to 50 μm.

8. The method of claim 1, wherein the particles have superhydrophobicity with a water contact angle of 125° or more.

9. The method of claim 1, wherein the particles have a BET specific surface area of 500 $m^2/g$ to 1500 $m^2/g$.

10. The method of claim 1, wherein the particles have a porosity of 90% or more.

11. The method of claim 1, wherein the particles comprise at least one selected from the group consisting of silica ($SiO_2$), alumina, carbon, and titania ($TiO_2$).

12. The method of claim 1, further comprising:
    checking anti-caking properties of the prepared superabsorbent polymer through caking testing, after the aging control treatment.

13. The method of claim 1, wherein the superabsorbent polymer is obtained by:
    polymerizing a monomer composition to prepare a hydrous gel polymer, wherein the monomer composition comprises a water-soluble ethylenic unsaturated monomer and a polymerization initiator, and wherein the polymerization is thermal polymerization or photopolymerization;
    drying the hydrous gel polymer;
    grinding the dried hydrous gel polymer to obtain superabsorbent polymer particles; and
    surface crosslinking the superabsorbent polymer particles using a surface crosslinking agent.

14. The method of claim 13, wherein the water-soluble ethylenic unsaturated monomer comprises any one or more selected from the group consisting of an anionic monomer and salts thereof, a nonionic hydrophilic monomer, and an amino group-containing unsaturated monomer and quaternary salts thereof.

15. The method of claim 13, wherein the polymerization is thermal polymerization, and the polymerization initiator comprises any one or more selected from the group consisting of a persulfate-based initiator, an azo-based initiator, hydrogen peroxide, and ascorbic acid.

16. The method of claim 13, wherein the polymerization is photopolymerization, and the polymerization initiator comprises any one or more selected from the group consisting of benzoin ether, dialkyl acetophenone, hydroxyl alkylketone, phenyl glyoxylate, benzyl dimethyl ketal, acyl phosphine, and α-aminoketone.

17. The method of claim 13, wherein the drying of the hydrogel polymer is at a temperature ranging from 150° C. to 250° C.

18. The method of claim 13, wherein the superabsorbent polymer particles, prior to surface crosslinking, have a particle size of 150-850 μm.

19. The method of claim 13, wherein the surface crosslinking agent comprises any one or more selected from the group consisting of a polyhydric alcohol compound; an epoxy compound; a polyamine compound; a haloepoxy compound; a haloepoxy compound condensed product; an oxazoline compound; a mono-, di- or poly-oxazolidinone compound; a cyclic urea compound; a polyhydric metal salt; and an alkylene carbonate compound.

20. The method of claim 1, wherein the superabsorbent polymer having improved anti-caking properties has a moisture content of 0.1 wt % or more.

21. The method of claim 1, wherein the adding step further comprises:
   adding the water to the superabsorbent polymer and the particles to form the composition consisting of the superabsorbent polymer, the particles, and the water.

* * * * *